US012642947B2

(12) United States Patent
Imran

(10) Patent No.: US 12,642,947 B2
(45) Date of Patent: Jun. 2, 2026

(54) INJECTION OF A THERAPEUTIC FORMULATION INTO A WALL OF THE GASTROINTESTINAL TRACT

(71) Applicant: Rani Therapeutics, LLC, San Jose, CA (US)

(72) Inventor: Mir A. Imran, Los Altos Hills, CA (US)

(73) Assignee: Rani Therapeutics, LLC, San Jose, CA (US)

( * ) Notice: Subject to any disclaimer, the term of this patent is extended or adjusted under 35 U.S.C. 154(b) by 923 days.

(21) Appl. No.: 17/890,009

(22) Filed: Aug. 17, 2022

(65) Prior Publication Data

US 2023/0088737 A1 Mar. 23, 2023

Related U.S. Application Data

(63) Continuation of application No. PCT/US2021/018399, filed on Feb. 17, 2021.

(Continued)

(51) Int. Cl.
*A61M 31/00* (2006.01)
*A61M 5/14* (2006.01)
(Continued)

(52) U.S. Cl.
CPC ........ *A61M 31/002* (2013.01); *A61M 5/1409* (2013.01); *A61M 5/155* (2013.01);
(Continued)

(58) Field of Classification Search
CPC ................ A61M 31/002; A61M 5/155; A61M 2005/14284; A61M 2210/1042;
(Continued)

(56) References Cited

U.S. PATENT DOCUMENTS 8,562,589 B2 10/2013 Imran
8,579,883 B2 11/2013 Tanaka et al.
(Continued)

FOREIGN PATENT DOCUMENTS

EP 1 884 259 A1 2/2008
EP 2 130 481 A1 12/2009
WO WO-2020/160399 A1 8/2020

*Primary Examiner* — Bradley J Osinski
(74) *Attorney, Agent, or Firm* — Foley & Lardner LLP

(57) ABSTRACT

A device includes an inflatable balloon, a reservoir disposed within the inflatable balloon, a needle compartment attached to the balloon and to the reservoir, an injection needle disposed within the needle compartment, and an inflation mechanism. The reservoir contains a therapeutic preparation. The inflation mechanism is structured to inflate the balloon, and upon inflation, the injection needle is structured to enter the reservoir. A method includes making an autoinjector available to a subject with instructions to ingest the autoinjector. The autoinjector is structured to inject a therapeutic preparation into a wall of a gastrointestinal tract of the subject responsive to ingestion of the autoinjector. The autoinjector includes an injection needle disposed in a needle compartment attached to a reservoir. The injection needle is initially separated from the reservoir, and is structured to enter the reservoir for delivery of the fluid therapeutic preparation through the needle into the wall.

21 Claims, 10 Drawing Sheets

Related U.S. Application Data

(60) Provisional application No. 63/020,811, filed on May 6, 2020, provisional application No. 62/978,222, filed on Feb. 18, 2020.

(51) Int. Cl.
    *A61M 5/142*         (2006.01)
    *A61M 5/155*         (2006.01)

(52) U.S. Cl.
    CPC .............. *A61M 2005/14284* (2013.01); *A61M 2207/10* (2013.01); *A61M 2210/1042* (2013.01)

(58) Field of Classification Search
    CPC ........ A61M 5/2046; A61M 2210/1053; A61M 2210/106
    See application file for complete search history.

(56) References Cited

U.S. PATENT DOCUMENTS

| | | | |
|---|---|---|---|
| 8,721,620 B2 | 5/2014 | Imran | |
| 8,734,429 B2 | 5/2014 | Imran et al. | |
| 8,759,284 B2 | 6/2014 | Imran | |
| 9,456,988 B2 | 10/2016 | Imran | |
| 9,757,514 B2 | 9/2017 | Imran et al. | |
| 9,757,548 B2 | 9/2017 | Imran | |
| 10,179,228 B2 | 1/2019 | Imran | |
| 10,252,039 B2 | 4/2019 | Imran | |
| 10,493,253 B2 | 12/2019 | Imran | |
| 10,596,359 B2 | 3/2020 | Imran | |
| 10,603,475 B2 | 3/2020 | Imran | |
| 10,632,251 B2 | 4/2020 | Imran et al. | |
| 11,253,686 B2 | 2/2022 | Imran | |
| 11,338,118 B2 | 5/2022 | Imran | |
| 11,376,405 B2 | 7/2022 | Imran | |
| 2004/0253304 A1* | 12/2004 | Gross | A61B 5/14539 424/451 |
| 2004/0267240 A1 | 12/2004 | Gross et al. | |
| 2007/0010709 A1 | 1/2007 | Reinschke | |
| 2008/0255543 A1* | 10/2008 | Tanaka | A61M 31/00 604/891.1 |
| 2014/0288535 A1 | 9/2014 | Raven et al. | |
| 2015/0064241 A1 | 3/2015 | Conrad | |
| 2019/0133937 A1 | 5/2019 | Imran et al. | |
| 2020/0289747 A1 | 9/2020 | Imran et al. | |
| 2022/0296510 A1 | 9/2022 | Imran | |
| 2022/0323733 A1 | 10/2022 | Imran | |

* cited by examiner

INJECTION OF A THERAPEUTIC FORMULATION INTO A WALL OF THE GASTROINTESTINAL TRACT

CROSS-REFERENCE TO RELATED APPLICATIONS

This application is a continuation of PCT/US2021/018399, filed Feb. 17, 2021, and claims benefit of priority to each of (i) U.S. Provisional Patent Application No. 62/978,222 titled GASTROINTESTINAL LIQUID AUTOINJECTION and filed on Feb. 18, 2020; and U.S. Provisional Patent Application No. 63/020,811 titled LIQUID INJECTION OF A THERAPEUTIC AGENT INTO A WALL OF THE GASTROINTESTINAL TRACT and filed on May 6, 2020; the aforementioned priority applications being hereby incorporated by reference in their respective entireties for all purposes.

BACKGROUND

Technical Field

Embodiments of the present disclosure relate to injection of one or more therapeutic formulations into a wall of the gastrointestinal tract. More specifically, embodiments of the present disclosure relate to swallowable autonomous delivery devices for injecting a fluid from a location within the gastrointestinal tract.

Background Discussion

While there has been an increasing development of therapeutic agents in recent years for the treatment of a variety of diseases and conditions, many of these require parenteral injection, including for many proteins, antibodies, and peptides.

Parenteral injection has a number of drawbacks, including pain of injection, risk of infection at the injection site, requirements for the use of sterile techniques during injection, and the requirement and associated risks of placing and maintaining an intravenous line in a subject for an extended period of time. While other delivery approaches have been employed such as implantable pumps, these approaches require semi-permanent implantation of a device, which has many limitations.

An inability to deliver many therapeutic agents orally can arise for a number of reasons, including poor oral toleration with complications including gastric irritation and bleeding, poor absorption of the therapeutic agents, or breakdown or degradation of compounds of the therapeutic agent in the stomach or intestines prior to absorption.

Delivery of a solid form dose using an ingestible delivery device has seen some success by way of injection of the solid form dose into a wall of the gastrointestinal tract; however, these devices may be limited to delivery of a few milligrams of a therapeutic agent. Some therapies require significantly higher dosing, so that a number or a frequency of required dosing events can make usage of these devices unattractive for convenience, cost, or other reasons.

Thus, there is a need for additional, alternative, and improved methods, devices, and articles for the oral delivery of therapeutic agents.

SUMMARY

Embodiments of the present disclosure include devices, systems and methods for auto-injection devices (which may be referred to herein as autoinjectors), for manufacturing autoinjectors, and for providing auto-injection of a therapeutic formulation in fluid form, delivered from within the gastrointestinal tract by an autoinjector. In various embodiments, the autoinjector is provided within an oral delivery device. In various embodiments, the autoinjector is provided with dosages of therapeutic agent sufficient for most therapeutic regimens. For example, an autoinjector may hold up to approximately 0.5 cubic centimeters (cc) of a therapeutic preparation, and the therapeutic preparation may include up to 200 milligrams (mg) or more of one or more therapeutic agents.

The autoinjector contains an injection needle. In an embodiment, the needle is sterile. In an embodiment, the injection needle degrades after use.

The autoinjector incorporates a balloon which is inflated by a gas, and the gas also provides pressure against a reservoir to eject fluid through the injection needle. The balloon may subsequently be deflated, and the balloon passes through the GI tract until it is expelled through the anus.

The autoinjector is housed in an outer shell, such as a capsule, which degrades in whole or in part at, above, or below a design threshold, such as degrading when a pH level is greater than 5.5. Breach of the outer shell due to degradation of the outer shell initiates an injection process which culminates by fluid being pushed out of the autoinjector through the injection needle into a wall of the GI tract (e.g., a wall of a lumen of the GI tract).

Further details of these and other embodiments and aspects are described more fully below, with reference to the attached drawings.

DETAILED DESCRIPTION

Embodiments of the present disclosure provide a swallowable device containing an autoinjector device for delivering a therapeutic preparation in fluid form into, or through, a wall of the gastrointestinal (GI) tract such as a wall of the stomach, or a wall of the small intestine or other lumen of the GI tract (a wall of the GI tract may be referred to herein as a "GIW"). In an embodiment, the medication is delivered through a mucosal layer of the GI tract (e.g., through the mucosa and into the submucosa, musculara, or serosa). In an embodiment, the medication is delivered through the GIW into the peritoneum or into the peritoneal cavity.

The devices, systems, and methods of the present disclosure are suited to delivering therapeutic preparations into a GIW even when digestive matter is present at a site of delivery.

Figure 1:
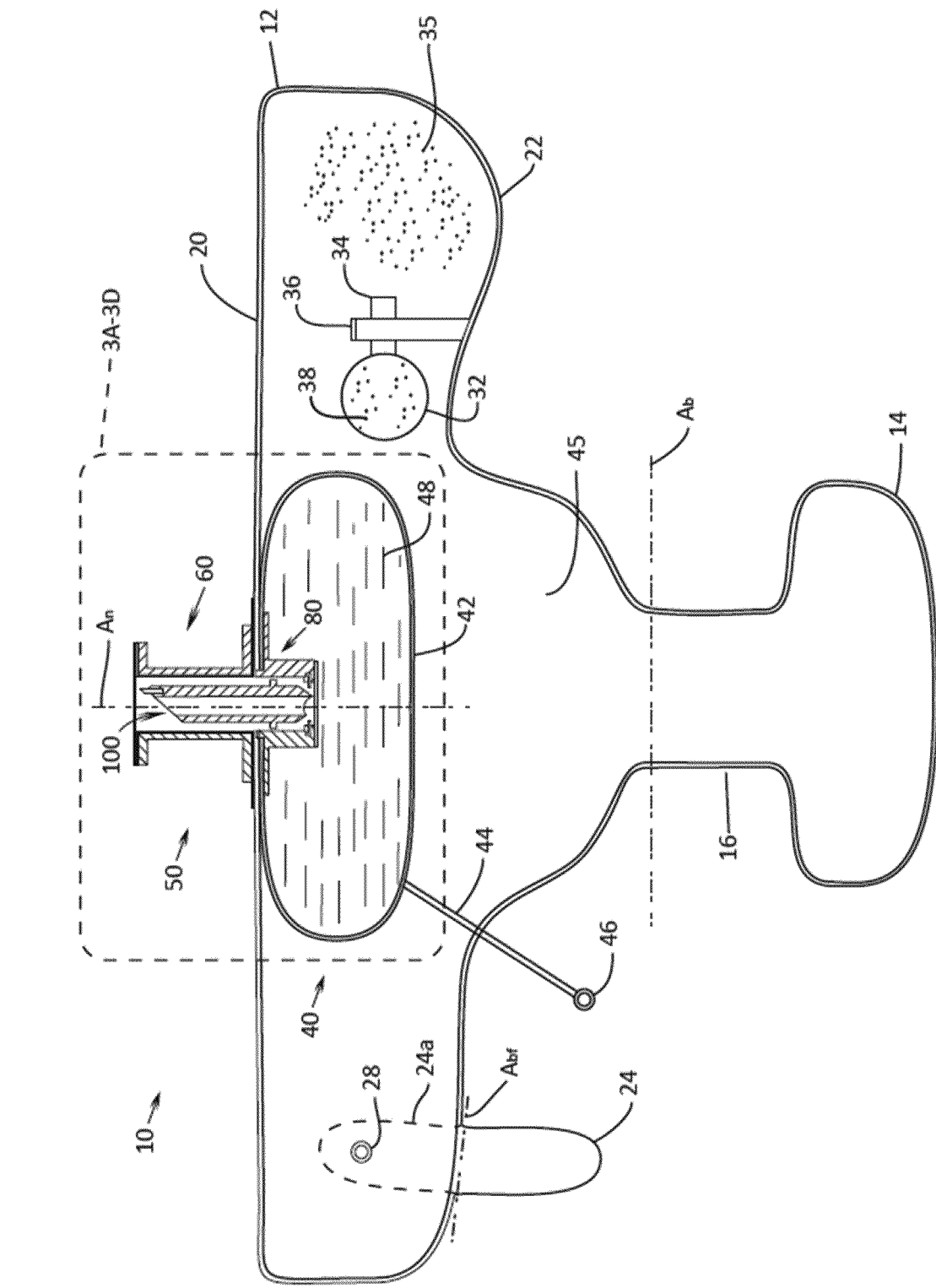
FIG. 1 illustrates an autoinjector device, according to one or more embodiments.

FIG. 1 illustrates an autoinjector device ("autoinjector 10"), according to one or more embodiments. The autoinjector 10 includes an expandable member in the form of an inflatable balloon 12, a deflation valve 28, a pouch 32, a conduit 34, a first reactant 38 contained within the pouch 32, a second reactant 35, a release valve 36, a reservoir 40, a fill port 46 coupled to the reservoir 40 by way of a tube 44, a fluid solution 48 contained in the reservoir 40, a needle compartment 50, and an injection needle 100. The autoinjector 10 is an automated injection device that can deliver one or more therapeutic preparations in fluid form upon the expansion of the balloon 12.

Not shown in the embodiment illustrated in FIG. 1 is an outer shell, such as, in some embodiments, a coating or a capsule, a coating over a capsule, or a capsule over a coating. The outer shell initially surrounds the autoinjector 10.

In an embodiment, the balloon 12 includes a pliable material selection such that when the balloon 12 is not inflated, the balloon 12 may be folded. Prior to addition of the outer shell, the balloon 12 may be folded and/or rolled to a suitable size (e.g., a size suitable for disposable in a 00-size capsule). In an embodiment, the outer shell includes a capsule and the balloon 12 is folded and/or rolled prior to being disposed in the capsule. In an embodiment, the outer shell includes a coating and the balloon 12 is folded and/or rolled prior to being coated.

The outer shell can protect the autoinjector 10 from a fluidic environment until the outer shell degrades. In an embodiment, the outer shell has a shape and composition to degrade at a pH level above about 5.5, commensurate to a pH level commonly found in the intestinal tract. In an embodiment, the outer shell has a shape and composition to degrade at a pH level lower than about 5.5, commensurate to a pH level commonly found in the stomach. Degradation of the outer shell may be in whole or in part, and may occur in stages. In an embodiment, the outer shell includes a size 00 capsule, 000 capsule, or other size capsule which degrades in the GI tract.

In an embodiment, the balloon 12 is structured with a material such that the balloon experiences some stretching during and/or after inflation. In an embodiment, the balloon 12 is structured with a material such that the balloon experiences minimal or insignificant stretching during and after inflation. A material of the balloon 12 may include multiple layers, where one or more layers provide for flexibility, and one or more layers provide a structure that minimizes or prevents stretching of another layer or other layers. In an embodiment, the balloon 12 includes a material having a first layer of a stretchable polymer (e.g., polyethylene), a second layer of nylon mesh, and a third layer of a stretchable polymer (e.g., polyethylene); where the nylon mesh is disposed between the stretchable polymer layers to minimize stretching of the balloon 12 during and after inflation. The stretchable polymer layers may provide for heat staking edges of the balloon 12 together to seal the balloon 12.

The balloon 12 is inflated by a gas produced by allowing mixing of the first reactant 38 with the second reactant 35. The pouch 32 containing the first reactant 38 is contained within an inner volume 45 of the balloon 12. The first reactant 38 is retained within the pouch 32 by constriction, pressure plug, or other sealing apparatus that is applied from the release valve 36 to the conduit 34. The balloon 12 contains the second reactant 35. In the illustration of FIG. 1, the second reactant 35 is located in a bulbous section 22 of the balloon 12 adjacent the conduit 34. In other embodiments, the second reactant 35 is additionally or alternatively elsewhere within the balloon 12. The conduit 34 is in fluid communication with both an inside volume of the pouch 32 and the inner volume 45 of the balloon 12.

In an embodiment, the release valve 36 includes a reaction valve, such that upon degradation of the outer shell and subsequent contact with a fluidic environment (e.g., digestive matter) via breach of fluid in the environment through a surface of the outer shell, the release valve 36 weakens or degrades, thus relieving pressure against the conduit 34. In an embodiment, the pouch 32 is a compliant balloon that is biased to compress when the conduit 34 opens upon release of pressure by the release valve 36, thereby ejecting the first reactant 38 through the conduit 34 into the inner volume 45 of the balloon 12. The first reactant 38 comes into contact and/or mixes with the second reactant 35 within the inner volume 45. In an embodiment, the two reactants are selected to react so as to cause a gas to form and pressurize the inner volume 45 and thereby inflate the balloon 12. The first reactant 38 and the second reactant 35 may be selected from a number of different biocompatible substances. In an embodiment, the first reactant 38 includes citric acid, and the second reactant 35 includes sodium bicarbonate or potassium bicarbonate, and the combination of the first reactant 38 with the second reactant 35 causes carbon dioxide to form, which serves to inflate the balloon 12.

The gas pressurizes the balloon 12 and expands the balloon 12 to an inflated state. The balloon 12 is shaped with a perimeter such that pressure within the balloon 12 aligns a long portion 20 of the balloon 12 against tissue at a delivery site (e.g., GIW).

The gas that pressurizes and expands the balloon 12 also applies pressure against the exterior of the reservoir 40 to force fluid in the reservoir 40 through the injection needle 100 and thus out of the autoinjector 10. As the balloon 12 inflates, pressure is exerted against a high percentage of the surface area of a membrane 42 of the reservoir 40, so that the membrane 42 is squeezed from many directions concurrently. This squeezing causes the fluid solution 48 contained in the reservoir 40 to be pushed into the injection needle 100 and subsequently injected through the injection needle 100 into tissue at a delivery site (e.g., GIW), as described in detail with respect to FIG. 3A-FIG. 3D.

The term "fluid" as used in the present disclosure refers to any solution that exhibits fluidic properties or can otherwise be forced from the reservoir 40 through the injection needle 100 by pressure on an outer surface of the reservoir 40. A fluid may be, for example, in the form of a gas, a liquid, a colloidal suspension, a gel, a slurry, a nanopowder, or a powder. A fluid can include a therapeutic preparation, a hydrating preparation, or other preparation, or a combination of preparations. In an embodiment, the reservoir 40 is structured to contain up to about 0.5 cc of fluid.

The fluid solution 48 in the reservoir 40 can include a therapeutic preparation. As discussed below, a therapeutic preparation may include one or more therapeutic agents. In an embodiment, the fluid solution 48 includes about 10 mg to about 15 mg of a therapeutic agent. In an embodiment, the fluid solution 48 includes up to about 50 mg of a therapeutic agent (e.g., about 10-40 mg, about 20-30 mg, about 10-50 mg, less than 50 mg, more than 10 mg). In other embodiments, the fluid solution 48 includes up to about 100 mg, up to about 200 mg, or more of a therapeutic agent.

The fluid solution 48 is propelled out of the autoinjector 10 through the injection needle 100. The injection needle 100 is positioned within a needle compartment 50. The needle compartment 50 includes two subassemblies, an upper chamber 60 and a lower chamber 80, that collectively define a cavity to house the injection needle 100. In an embodiment, the cavity has a longitudinal axis in alignment with, or substantially coincident with, a longitudinal axis ($A_n$) of the injection needle 100. The upper chamber 60 and the lower chamber 80 may be one contiguous structure, or may be, as illustrated in FIG. 1, separate structures. The embodiment of the autoinjector 10 illustrated in FIG. 1 employs the upper chamber 60 being disposed on an outer surface of the balloon 12, with the lower chamber 80 being positioned inside the balloon 12 and inside a membrane 42 of the reservoir 40 so as to be at least partially submersed in the fluid solution 48.

After the fluid solution 48 has been expelled from the reservoir 40, it may be desirable to deflate the balloon 12 to expedite movement of the balloon 12 through the GI tract towards the rectum and thereby expulsion from the body faster than would be probable if the balloon 12 remained inflated. The deflation valve 28 is provided to cause deflation of the balloon 12 upon completion of an injection. In an embodiment, the deflation valve 28 includes a reaction valve that includes an action mechanism whereby fluid entering through the breached outer shell causes the deflation valve 28 to open and release the gas from within the balloon 12. In an embodiment, multiple deflation valves 28 may be included in the autoinjector 10 at various locations on the balloon 12. The deflation valve 28 may be, for example, in similar form to the release valve 36, such that the deflation valve 28 degrades to open a channel (not shown) for the gas to exit the balloon 12. In another example, the deflation valve 28 may be a degradable cover disposed over a hole in the balloon 12 such that gas may exit the balloon 12 through the hole when the cover degrades.

The deflation valve 28 is designed to withstand breach until after injection of the fluid solution 48 from the reservoir 40 is complete. To ensure against premature breach of the deflation valve 28, an optional flap 24 may be disposed over the deflation valve 28 while the balloon 12 is in a folded (non-inflated) state. This provides a barrier to fluid ingress toward the deflation valve 28, and thus ensures a delay of degradation and breach of the deflation valve 28 at least until after the balloon 12 is inflated. The inflating of the balloon 12 and the corresponding injection of the fluid solution 48 at the delivery site occurs quickly (e.g., seconds) after breach of the outer shell, so that, in an embodiment, delaying a breach of the deflation valve 28 by design of the deflation valve 28, and/or by covering the deflation valve 28 with a folded portion of the balloon 12 until the balloon 12 is inflated, is sufficient without use of the flap 24 to ensure that deflation occurs subsequent to injection.

In an embodiment, the flap 24 is taped, tacked or otherwise adhered to a position 24a while the balloon 12 is folded. Upon inflation of the balloon 12, a rounding of the perimeter of the balloon 12, due to the inflation, forces the adherence of the flap 24 to the position 24a to release and bend the flap 24 about an axis (e.g., $A_{bf}$) from the position 24a toward the location shown in FIG. 1. This exposes the deflation valve 28 to the fluidic environment of the GI tract to then begin degradation of the deflation valve 28. Once the deflation valve 28 has degraded to an extent that gas begins to release from the inner volume 45 of the balloon 12, the balloon 12 will quickly (e.g., seconds or less than a second) deflate to a large extent and will thus pass more easily through the GI tract.

In FIG. 1, a sizing member 14 is positioned on an opposite side of a hinge portion 16 from the long portion 20 of the balloon 12. In an embodiment, a selected material of the balloon 12 is not significantly stretchable, so that inflation of the balloon 12 builds pressure within the inner volume 45 of a main body of the balloon 12 that includes the long portion 20, and builds pressure within the sizing member 14. Accordingly, the main body of the balloon 12 and the sizing member 14 become largely non-compliant (e.g., fairly rigid) when inflated. The hinge portion 16 may remain compliant due its narrow dimension(s) (e.g., width, depth, and/or diameter), even when the balloon 12 is otherwise fully inflated.

Depending on an interior circumference of the delivery site (e.g., an interior circumference of a lumen of the GI tract), the hinge portion 16 may remain partially folded (e.g., around a fold line $A_b$), or may extend fully. In this manner, the balloon 12 can self-adjust to the particular dimensions of the delivery site (e.g., internal dimensions of the GI tract of a particular subject), and a single size of the balloon 12 may be sufficient for all of, or many of, quite different subjects (e.g., different sizes of humans, different sexes or ages of subjects, and/or different animalia species). In an embodiment, an autoinjector in accordance with the present disclosure is designed to be delivered folded within a 00-sized capsule or a 000-sized capsule, and the same design is used for dogs, pigs, monkeys, and humans.

By way of example, when the delivery site is within an intestinal lumen, an outer perimeter of the balloon 12 when inflated pushes against tissue surfaces in the lumen (e.g., the sizing member 14 and the long portion 20 push against inner walls of the lumen) with a force sufficient to maintain the balloon 12 aligned at the delivery site for a time or until deflation. With no obstacle to its expansion, the balloon 12 would assume a fully inflated configuration. If, however, the balloon 12 encounters resistance during inflation, such as by an internal circumference of the lumen being less than a maximum fully inflated dimension of the balloon 12, the hinge portion 16 may remain somewhat unfolded (e.g., will assume an arcuate or angular shape between the sizing member 14 and the main body of the balloon 12). In this manner, the balloon 12 inflates to a size sufficient to hold the balloon 12 in position for delivery of the fluid solution 48, so that a same sized balloon 12 may be used for a broad range of lumen internal circumferences.

The sizing member 14 can contact one portion of the GI tract wall and urge an opposing side of the balloon 12 (e.g., the long portion 20, or a portion adjacent to the long portion 20) against another portion of the GI tract wall. This serves to align and position the needle compartment 50 and the injection needle 100 in approximately perpendicular orientation against the GIW, and from there, the needle compartment 50 may be actuated to advance the injection needle 100 into the GIW for delivery of the fluid solution 48.

An autoinjector of the present disclosure can take on a variety of different physical forms. One form is illustrated in FIG. 1 by way of example, and a few other forms are illustrated in FIGS. 2A-2D by way of further examples.

FIGS. 2A-2D illustrate various embodiments of the autoinjector 10 of FIG. 1. In FIG. 2A, FIG. 2B, FIG. 2C, FIG. 2D: the embodiments of the autoinjector 10 are referenced as autoinjectors 10A, 10B, 10C, 10D, respectively; the embodiments of the balloon 12 are referenced as balloons 12a, 12b, 12c, 12d, respectively; the embodiments of the sizing member 14 are referenced as sizing members 14a, 14b, 14c, 14d, respectively; and the embodiments of the hinge portion 16 are referenced as hinge portions 16a, 16b, 16c, 16d, respectively.

Figure 2A:
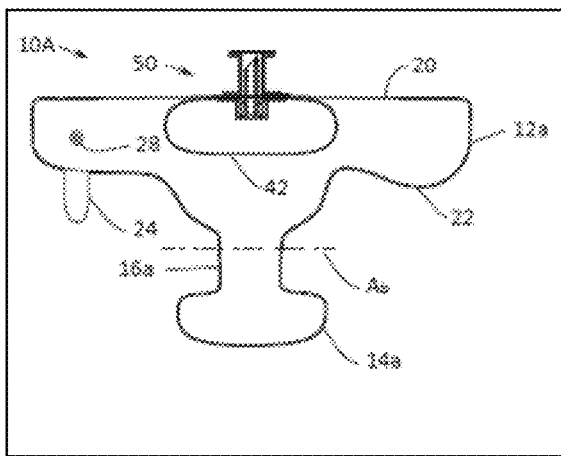
FIG. 2A illustrates an embodiment of an autoinjector device.

In the autoinjector 10A of FIG. 2A, the balloon 12a includes an expandable main body (with long portion 20) joined to the sizing member 14a by the narrower hinge portion 16a. The sizing member 14a is generally smaller than the main balloon body to minimize internal volume of the balloon 12a. The sizing member 14a is large enough such that the sizing member 14a in conjunction with the main balloon body can provide alignment/purchase with a lumen wall (e.g., GIW), to retain the balloon 12a in position at a delivery site.

Figure 2B:
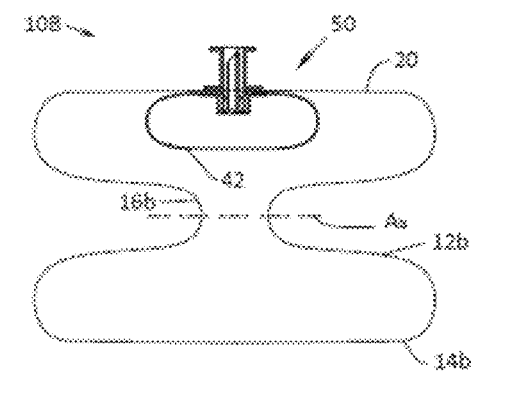
FIG. 2B illustrates another embodiment of an autoinjector device.

In the autoinjector 10B of FIG. 2B, the balloon 12b includes an expandable main balloon body (with long portion 20) joined to the sizing member 14b by the hinge portion 16b. The sizing member 14b is similar in size to the main balloon body.

Figure 2C:
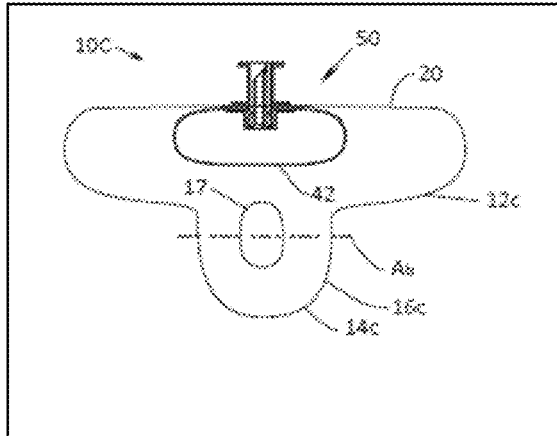
FIG. 2C illustrates another embodiment of an autoinjector device.

In the autoinjector 10C of FIG. 2C, the balloon 12c includes an expandable main balloon body (with long portion 20) joined to the sizing member 14c by the hinge portion 16c having an aperture 17 to minimize internal volume of the balloon 12 while providing a surface area to provide alignment/purchase with a lumen wall (e.g., GIW).

Figure 2D:
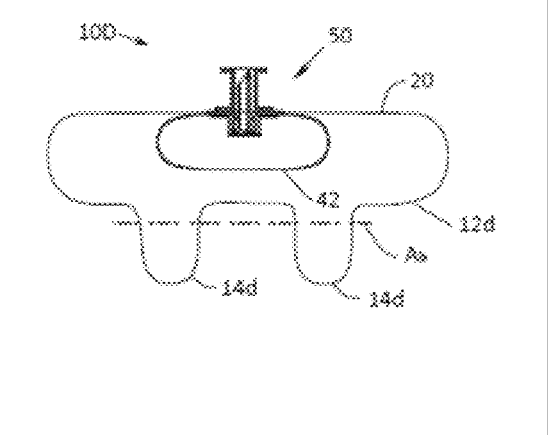
FIG. 2D illustrates another embodiment of an autoinjector device.

In the autoinjector 10D of FIG. 2D, the balloon 12d includes an expandable main balloon body (with long portion 20) and a pair of sizing members 14d. The pair of sizing members 14d may provide for disposition against an uneven inner circumference of the delivery site, and/or may provide for improved alignment/purchase with a lumen wall (e.g., GIW).

FIGS. 3A-3D illustrate enlarged cross-sectional views of a portion of the autoinjector 10 of FIG. 1 indicated approximately by the dotted square in FIG. 1 marked "3A-3D". The enlarged views include the needle compartment 50 and the reservoir 40 having an inner volume 49 filled with the fluid solution 48. The autoinjector 10 is illustrated in FIGS. 3A-3D during various stages of deployment.

Figure 3A:
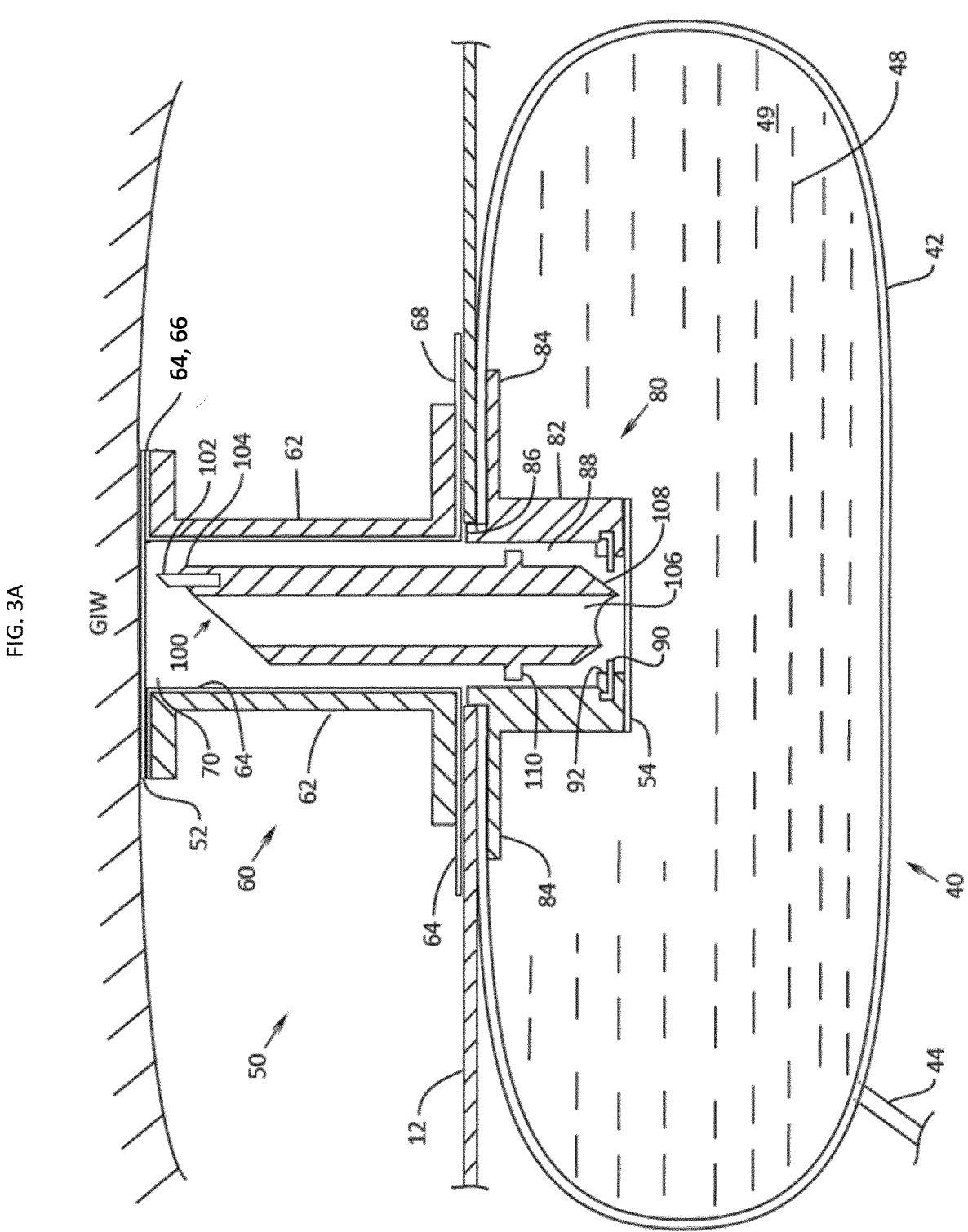
FIG. 3A illustrates an embodiment of an autoinjector device of FIG. 1.

In FIG. 3A, the needle compartment 50 is illustrated disposed adjacent a GIW after degradation of the outer shell or capsule, and after inflation of the balloon 12. The inflation of the balloon 12 may occur quickly (e.g., within seconds) after the autoinjector 10 is exposed to a fluidic environment, and the inflation may be rapid (e.g., less than a second) after the release valve 36 is breached to release the first reactant 38 within the balloon 12.

The upper chamber 60 of the needle compartment 50 includes a collar 62 and a collapsible tube 64. The collar 62 and the collapsible tube 64 provide protection of the injection needle 100 during manufacture, storage, shipping, handling, and oral delivery of the autoinjector 10. The collar 62 also provides support for and protection of the collapsible tube 64 during manufacture, storage, shipping, handling, and oral delivery of the autoinjector 10. The collar 62 may be disposed around (e.g., formed around or placed around) the collapsible tube 64, such as via casting, injection molding, deposition, or other process. The collar 62 is at least partially formed of a degradable material that begins degradation when fluid contacts the collar 62 after breaching the outer shell surrounding the autoinjector 10. The autoinjector 10 is designed in a manner such that a structural integrity and strength of the collar 62 is quickly and significantly diminished by degradation upon exposure to a fluidic environment. In an embodiment, the collar 62 is formed from, or includes, a polyvinyl pyrolidone (e.g., Polyplasdone™ polymer available from Ashland).

The collapsible tube 64 includes an upper flange 66 and a lower flange 68, each of which may be either integrally formed with or attached to the collapsible tube 64. The lower flange 68 provides a surface for the collapsible tube 64 to be coupled with the balloon 12, such as by adhesive, hot stake, or other attachment.

An upper seal 52 is affixed to the collapsible tube 64 along an outer surface of the upper flange 66. The upper seal 52 and the collapsible tube 64 together seal off an upper extent 70 of a cavity 88. In an embodiment, the upper seal 52 is a thin film of aluminum foil that is affixed to the collapsible tube 64, such as with a biocompatible adhesive, or by hot stake.

The collapsible tube 64 as supported by the collar 62 provides a structure for protection of the injection needle 100. The collapsible tube 64 is constructed in a manner such that it collapses easily under vertical pressure when not supported by the collar 62. For example, a material used to form the collapsible tube 64 may be thin, and/or formed in a pattern (e.g., honeycomb, strips, lattice, or herringbone), such that it collapses under pressure.

The lower chamber 80 of the needle compartment 50 includes a tubular body 82 extending into the balloon 12 and the reservoir 40. The tubular body 82 includes an upper flange 84 structured to couple (e.g., with adhesive, hot stake, or other attachment) to the membrane 42 at a boss 86. The lower chamber 80 includes an inner boss 92 that acts as a stop to downward motion of the injection needle 100 by means of a protrusion 110 on an outer surface of the injection needle 100. The protrusion 110 extends partially or fully circumferentially around the injection needle 100, and may be formed integrally with, or added to, the injection needle 100. The inner boss 92 extends partially or fully circumferentially around an inner circumference of the tubular body 82. The inner boss 92 and the protrusion 110 are designed in a manner such that movement of the injection needle 100 through the tubular body 82 of the lower chamber 80 is halted when the protrusion 110 encounters the inner boss 92.

In an embodiment, the lower chamber 80 includes a gasket, O-ring or other elastomeric radial shaft seal 90 that has an inner diameter smaller than or at least matching an outer diameter of the injection needle 100.

A bottom surface of the tubular body 82 is capped by a lower seal 54 affixed to the tubular body 82. In an embodiment, the lower seal 54 is a thin film of aluminum foil that is affixed to the tubular body 82, such as by adhesive, hot stake, or other attachment.

The cavity 88 is defined by the upper chamber 60 and the lower chamber 80. The collapsible tube 64, the tubular body 82, the upper seal 52, and the lower seal 54, together with the balloon 12 and the membrane 42, maintain the cavity 88 in a closed environment prior to injection. Thus, if the needle compartment 50, the injection needle 100, the reservoir 40, and the balloon 12 were assembled in a manner such that the cavity 88 and the injection needle 100 were initially sterile, the injection needle 100 can remain sterile in the cavity 88 until the injection needle 100 is deployed.

In an embodiment, the cavity 88 is largely defined by substantially cylindrical inner surfaces of the collapsible tube 64 of the upper chamber 60 and the tubular body 82 of the lower chamber 80, such that the cavity 88 has a substantially circular perimeter in a cross-section of the needle compartment 50. In other embodiments, a perimeter of the cavity 88 in a cross-section of the needle compartment 50 has a shape other than circular.

In an embodiment, the tubular body 82 is formed of a polymer such as polyethylene (PE). In an embodiment, the collapsible tube 64 is formed of a polymer such as PE.

Figure 3B:
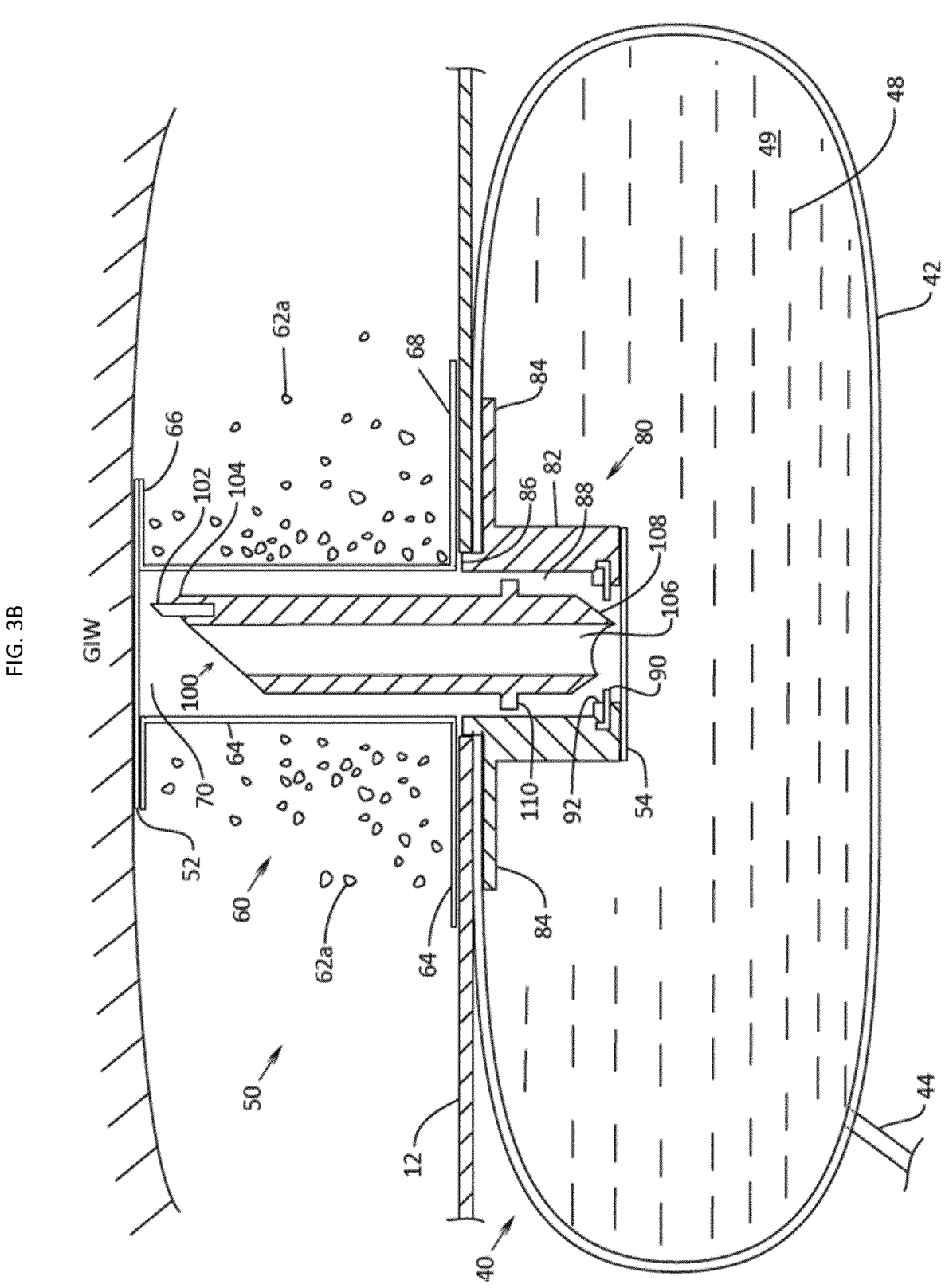
FIG. 3B illustrates an embodiment of an autoinjector device of FIG. 1 after degradation of at least a portion of a collar of a needle compartment of the autoinjector.
Figure 3C:
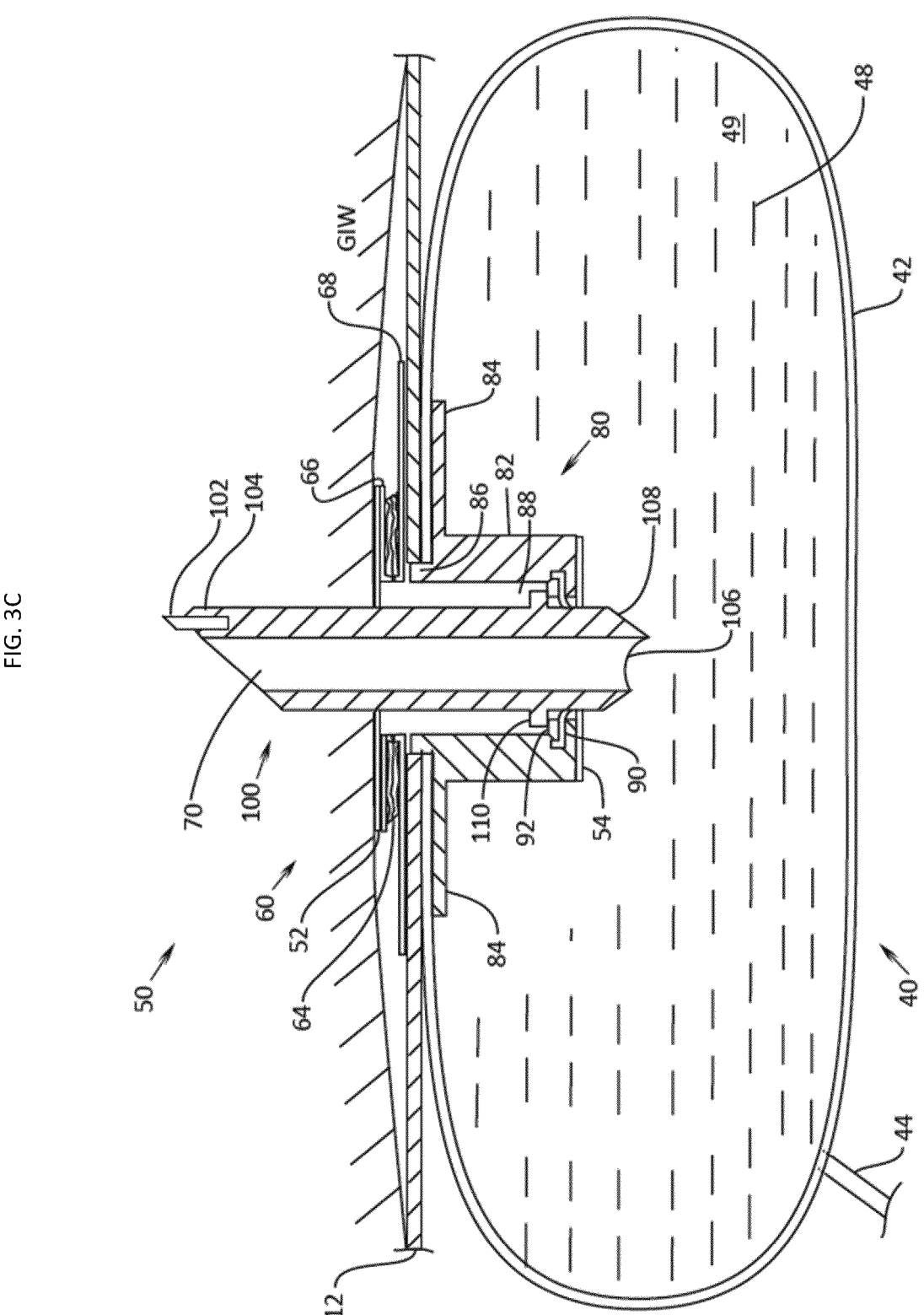
FIG. 3C illustrates an embodiment of an autoinjector device of FIG. 1 after collapse of a collapsible tube of the needle compartment.
Figure 3D:
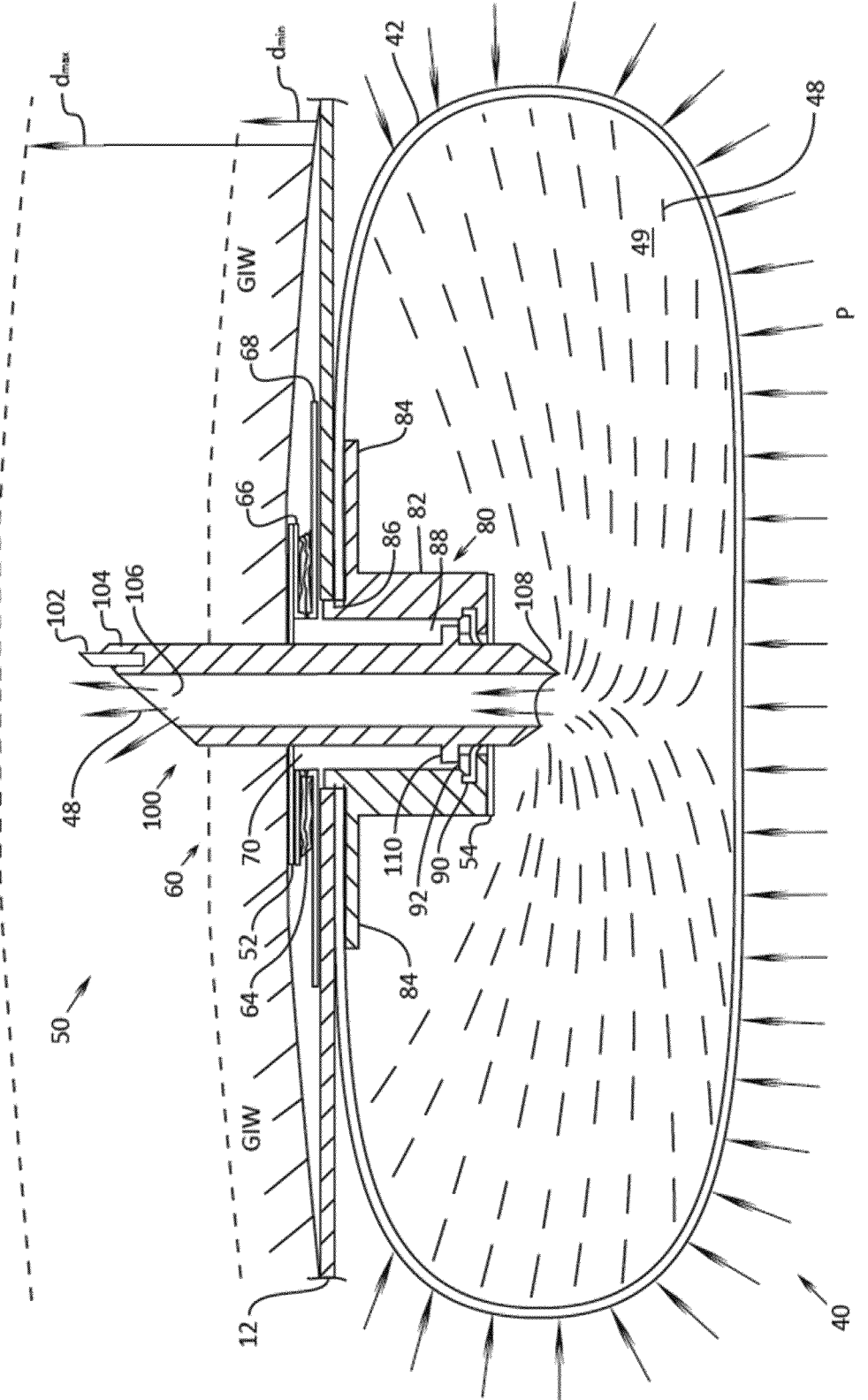
FIG. 3D illustrates an embodiment of an autoinjector device of FIG. 1 during injection of a therapeutic preparation into the GI tract.
Figure 4:
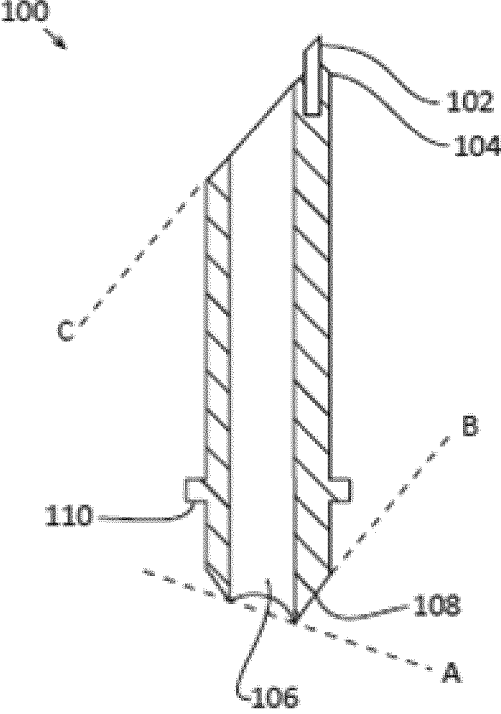
FIG. 4 illustrates an embodiment of a degradable injection needle.

An embodiment of the injection needle 100 is illustrated in FIGS. 3A-3D, and is also shown in isolation in FIG. 4. In this embodiment, the injection needle 100 has a tubular shape with a central channel 106 extending between a distal end 104 and a proximal end 108. The distal end 104 terminates at a sharp tip 102 so as to provide a piercing action when ejected from the needle compartment 50. In an embodiment, the sharp tip 102 is formed in a material used in a remainder of the injection needle 100. In an embodiment, the sharp tip 102 is an insert of material differing from a material in a remainder of the injection needle 100. For example, the sharp tip 102 may be any hard material, such as a metal. In an embodiment, the sharp tip 102 is formed of magnesium, which is degradable. The remainder of the injection needle 100 may be composed of a degradable material.

The proximal end 108 of the injection needle 100 may be angled as shown by a dotted line A. Further, an outer surface of the proximal end 108 of the injection needle 100 may be beveled as shown by a dotted line B. The angle and bevel separately and in combination can provide a cutting edge to pierce the lower seal 54. The distal end 104 of the injection needle 100 may be angled as shown by a dotted line C and may additionally or alternatively be beveled. The angle and bevel separately and in combination can provide a cutting edge to pierce the upper seal 52. The angled distal end 104 and the sharp tip 102 also aid in piercing/penetrating tissue at a delivery site.

FIG. 3A illustrates an initial configuration of the autoinjector 10 prior to degradation of the collar 62 of the needle compartment 50 due to exposure to fluid in the GI tract. At this stage, the outer shell of the autoinjector 10 has sufficiently degraded to allow fluid to breach the outer shell and reach the release valve 36 to initiate expansion of the balloon 12. Accordingly, the upper seal 52 is shown positioned adjacent the GIW in an orientation suitable for delivering the fluid solution 48 into the GIW. Although not shown, portions of the outer shell may still remain at this stage, including between the upper seal 52 and the GIW. The collar 62 of the upper chamber 60 continues to provide support for the collapsible tube 64.

FIGS. 3B-3D illustrate a progression of the autoinjector 10 during (FIG. 3B) and subsequent to (FIGS. 3C-3D) degradation of the collar 62.

In FIG. 3B, the autoinjector 10 is depicted during degradation of the collar 62. At this stage, fluid from the GI tract has reached the collar 62 and has begun the degradation. The collar 62 may degrade into pieces or particles 62a as depicted in FIG. 3B, or may additionally or alternatively degrade by weakening such that the collar 62 no longer provides sufficient support to maintain the collapsible tube 64 in its initial form (e.g., a cylindrical form). In an embodiment, the collar 62 includes a quickly degrading material (e.g., poly(vinyl alcohol) (PVA), polyvinyl pyrrolidone, or the like) that is susceptible to degradation when exposed to fluid, and in particular fluids that are present in the GI tract.

In FIG. 3C, as the balloon 12 continues to inflate and presses the needle compartment 50 against tissue at the delivery site (e.g., GIW), the degraded or partially degraded collar 62 provides minimal resistance due its state of degradation, diminishing its support of the collapsible tube 64. The collapsible tube 64 collapses due to the vertical pressure exerted on the needle compartment 50 between the balloon 12 and tissue at the delivery site. As the collapsible tube 64 is collapsing, the injection needle 100 is forced through the upper seal 52 and the lower seal 54 simultaneously or sequentially, with the distal end 105 of the injection needle 100 breaching (e.g., piercing) the upper seal 52 and the proximal end 108 of the injection needle 100 breaching (e.g., piercing) the lower seal 54. The injection needle 100 is encouraged to advance into tissue at the delivery site, by being blocked by the stopping function provided by the inner boss 92 of the lower chamber 80 in concert with the protrusion 110 of the injection needle 100. The radial shaft seal 90 comes into contact with the injection needle 100 as the proximal end 108 of the injection needle 100 approaches the lower seal 54. The proximal end 108 breaches the lower seal 54 and enters the reservoir 40; the radial shaft seal 90 blocks the fluid solution 48 from exiting the reservoir 40 through the cavity 88 around an outside perimeter of the injection needle 100.

In FIG. 3D, after the lower seal 54 has been breached by the proximal end 108 of the injection needle 100, pressure P exerted on an outer surface of the membrane 42 of the reservoir 40 by the buildup of pressure inside the balloon 12 causes compression of the reservoir 40 and subsequent flow of the fluid solution 48 (containing one or more therapeutic preparations) from the reservoir 40 into the channel 106 of the injection needle 100. If or when the upper seal 52 has been breached by the distal end 104 of the injection needle 100, the fluid solution 48 is delivered into tissue at the delivery site. The radial shaft seal 90 remains in contact with the injection needle 100, blocking the fluid solution 48 from exiting the reservoir 40 through the cavity 88 around an outside perimeter of the injection needle 100.

In an embodiment, one or more of the injection needle 100, components of the upper chamber 60 and/or the lower chamber 80, or other components of the autoinjector 10 comprise a biodegradable material or a combination of biodegradable materials. Examples of biodegradable materials include biodegradable polymers, cellulose, sugar, and maltose. Examples of biodegradable polymers include poly-ethylene oxide (PEO), poly(lactic acid) (PLA), poly(glycolic acid) (PGA), or a combination of PLA and PGA such as poly(lactic-co-glycolic acid) (PLGA) or poly(glycolide-co-lactide) (PGLA).

An embodiment of a method to manufacture the autoinjector 10 is described next.

A bottom housing segment (e.g., the lower chamber 80) is provided. A lower seal (e.g., the lower seal 54) is affixed to the bottom housing segment.

The bottom housing segment (with lower seal) is disposed in and affixed to a reservoir (e.g., the reservoir 40), and the combination of the bottom housing segment and the reservoir is disposed in and affixed to an expandable member (e.g., the balloon 12).

A collapsible tube (e.g., the collapsible tube 64) is attached to the expandable member and/or to the bottom housing segment. In an embodiment, the collapsible tube is formed of PE.

A collar (e.g., the collar 62) is disposed around the collapsible tube. In an embodiment, the collar is formed of PVA or polyvinyl pyrolidone.

A needle (e.g., the injection needle 100) is disposed within a cavity formed collectively by the bottom housing segment and the collapsible tube.

A seal (e.g., the upper seal 52) is affixed to the collapsible tube. A reservoir (e.g., the reservoir 40) is filled with a therapeutic preparation through a port (e.g., through the fill port 46 and the tube 44 in FIG. 1).

After filling the reservoir, the expandable member is sealed completely around its perimeter, such as by heat staking. The completed seal cuts off the port (e.g., cuts off the fill port 46 and the portion of the tube 44 extending outside of the expandable member, thus sealing the tube 44).

Reactants and associated assemblies (e.g., the pouch 32 with the first reactant 38, the conduit 34, and the second reactant 35) may be added to the expandable member at any manufacturing stage before the expandable member is fully sealed. Further, the expandable member may be partially sealed at any manufacturing stage, with the seal completed after filling the reservoir.

FIGS. 5-10 illustrate an embodiment of a method of manufacture of a swallowable device for delivering medication in fluid form.

Figure 5:
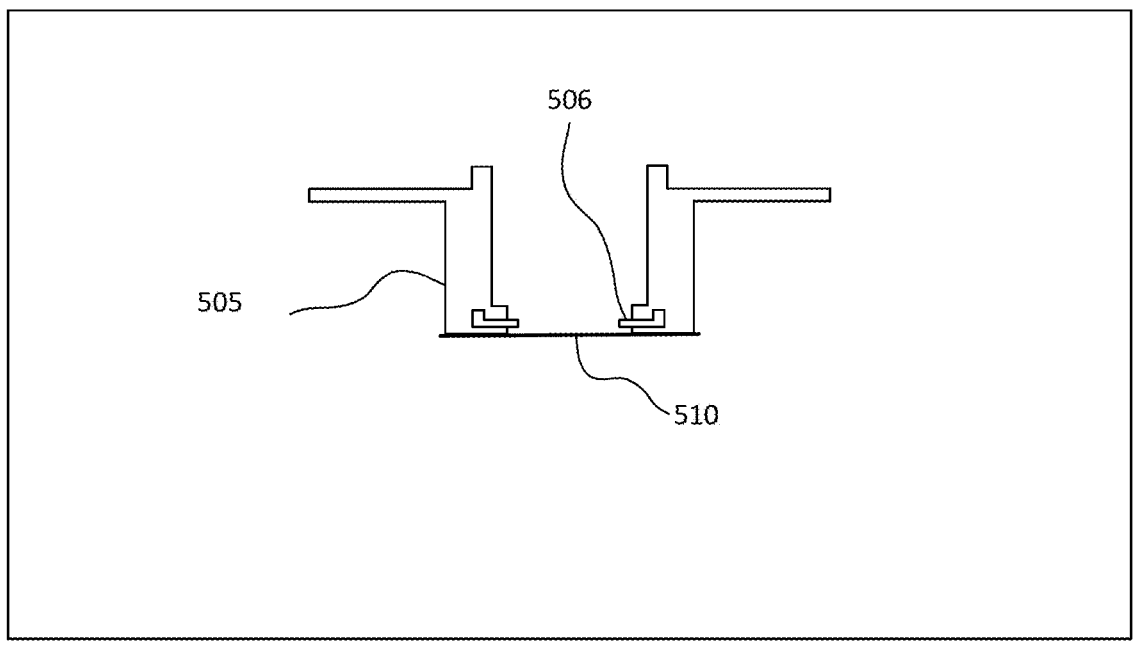
FIG. 5 illustrates an aspect of an embodiment of a method of manufacture of an autoinjector device for delivering a therapeutic preparation in fluid form.

In FIG. 5, a bottom housing segment 505 is provided, incorporating a radial shaft seal 506. A seal 510 is affixed to the bottom housing segment 505. In an embodiment, the bottom housing segment 505 may be formed of PE, the radial shaft seal 506 may be formed of an elastomer, and the seal 510 may be formed of an aluminum foil.

Figure 6:
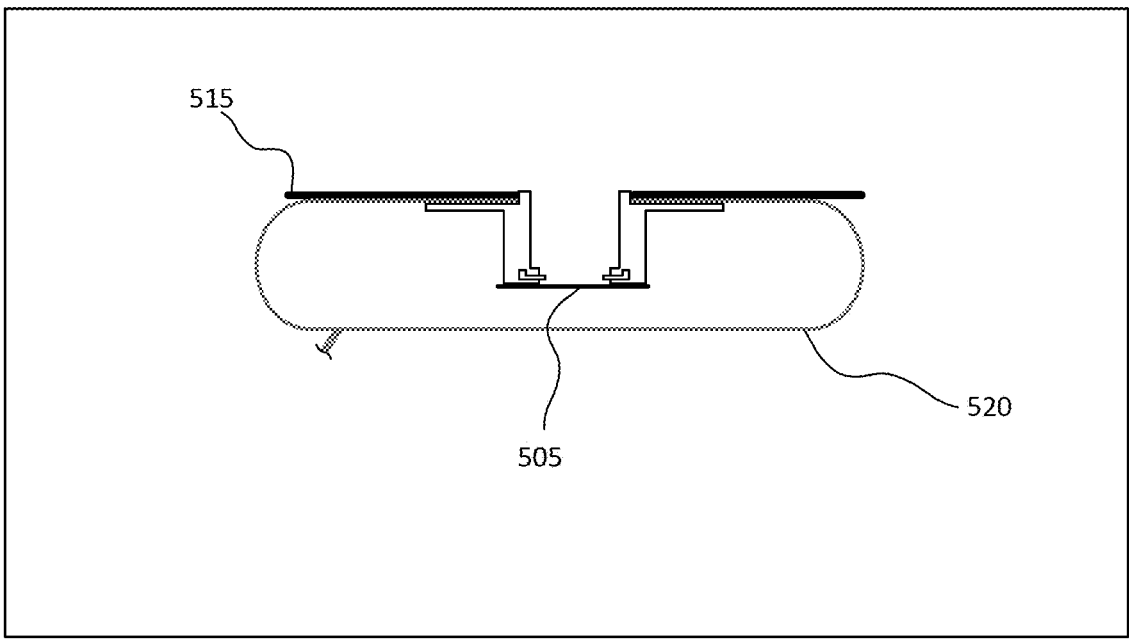
FIG. 6 illustrates another aspect of an embodiment of a method of manufacture of an autoinjector device for delivering a therapeutic preparation in fluid form.

In FIG. 6, the bottom housing segment 505 (with the radial shaft seal 506 and the seal 510) is disposed within and affixed to a reservoir 520, and the combination of the bottom housing segment 505 and the reservoir 520 is disposed within and affixed to a balloon 515.

Figure 7:
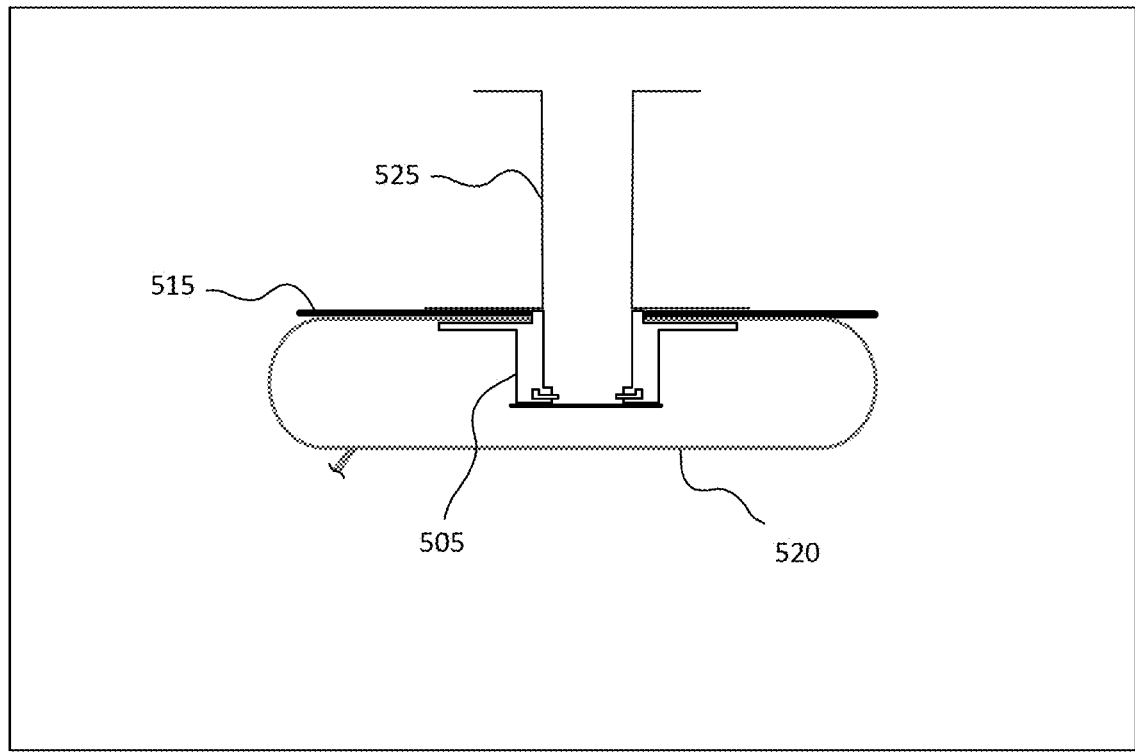
FIG. 7 illustrates another aspect of an embodiment of a method of manufacture of an autoinjector device for delivering a therapeutic preparation in fluid form.

In FIG. 7, a collapsible tube 525 is attached to the balloon 515 and the bottom housing segment 505. In an embodiment, the collapsible tube 525 is formed of PE.

Figure 8:
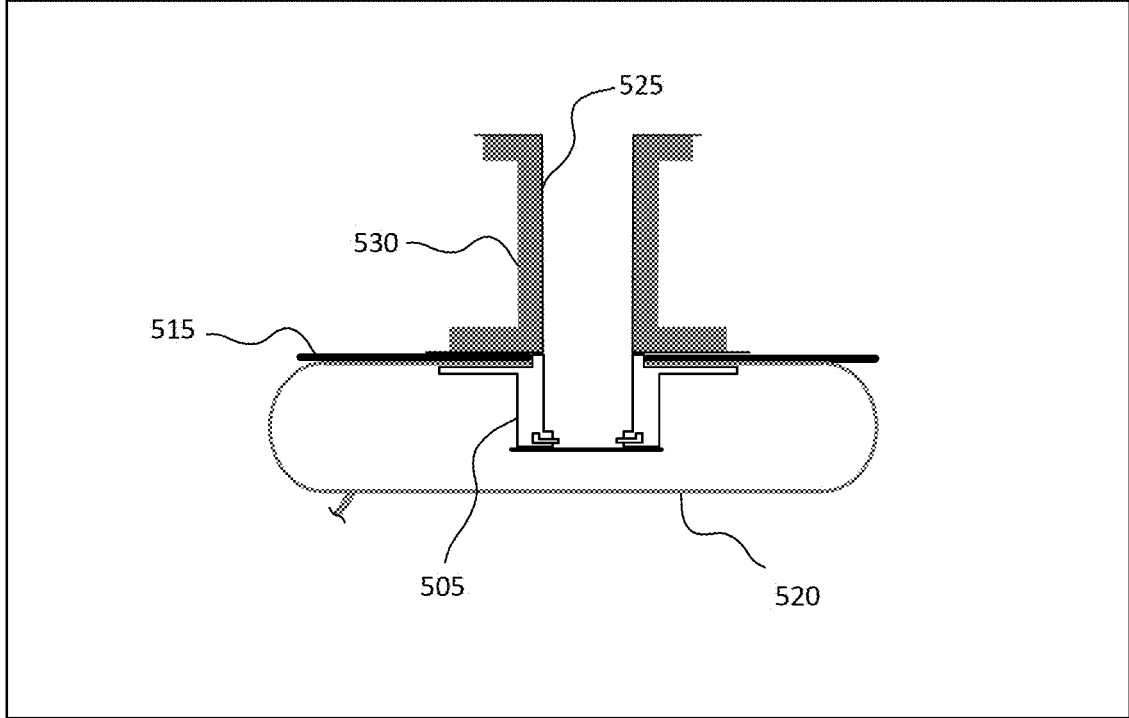
FIG. 8 illustrates another aspect of an embodiment of a method of manufacture of an autoinjector device for delivering a therapeutic preparation in fluid form.

In FIG. 8, a collar 530 is disposed around the collapsible tube 525. In an embodiment, the collar 530 is formed of PVA or polyvinyl pyrolidone.

Figure 9:
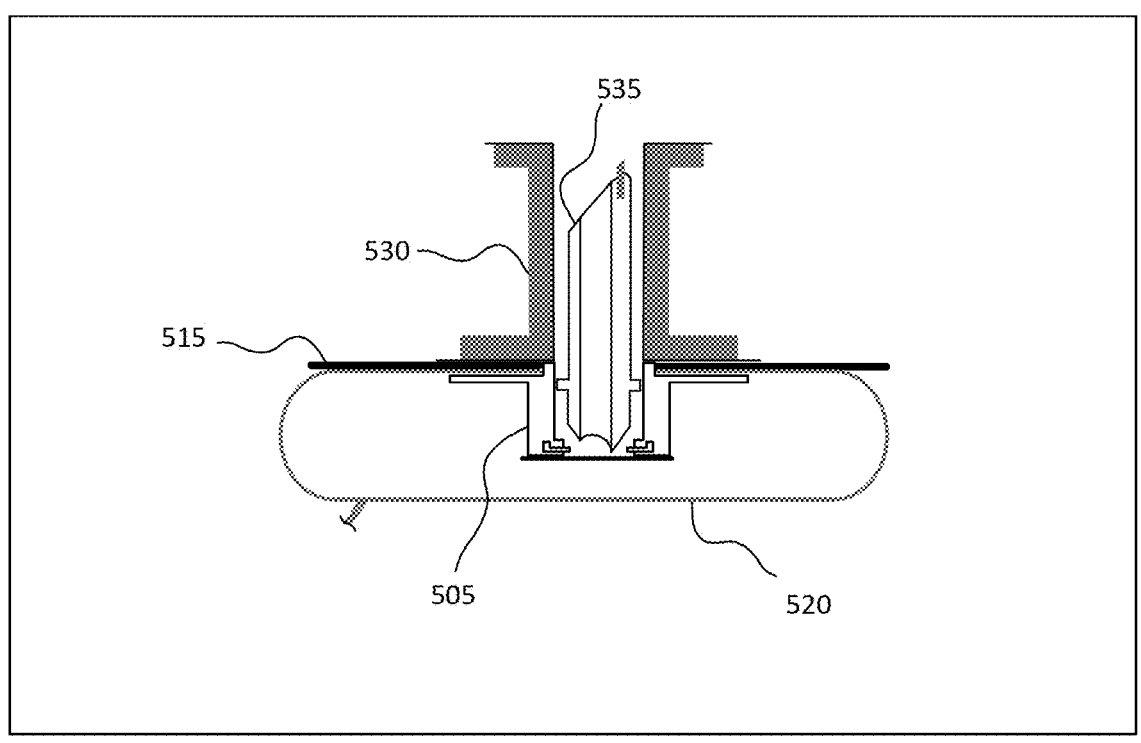
FIG. 9 illustrates another aspect of an embodiment of a method of manufacture of an autoinjector device for delivering a therapeutic preparation in fluid form.

In FIG. 9, an injection needle 535 is disposed within a cavity defined by the bottom housing segment 505 and the collapsible tube 525.

Figure 10:
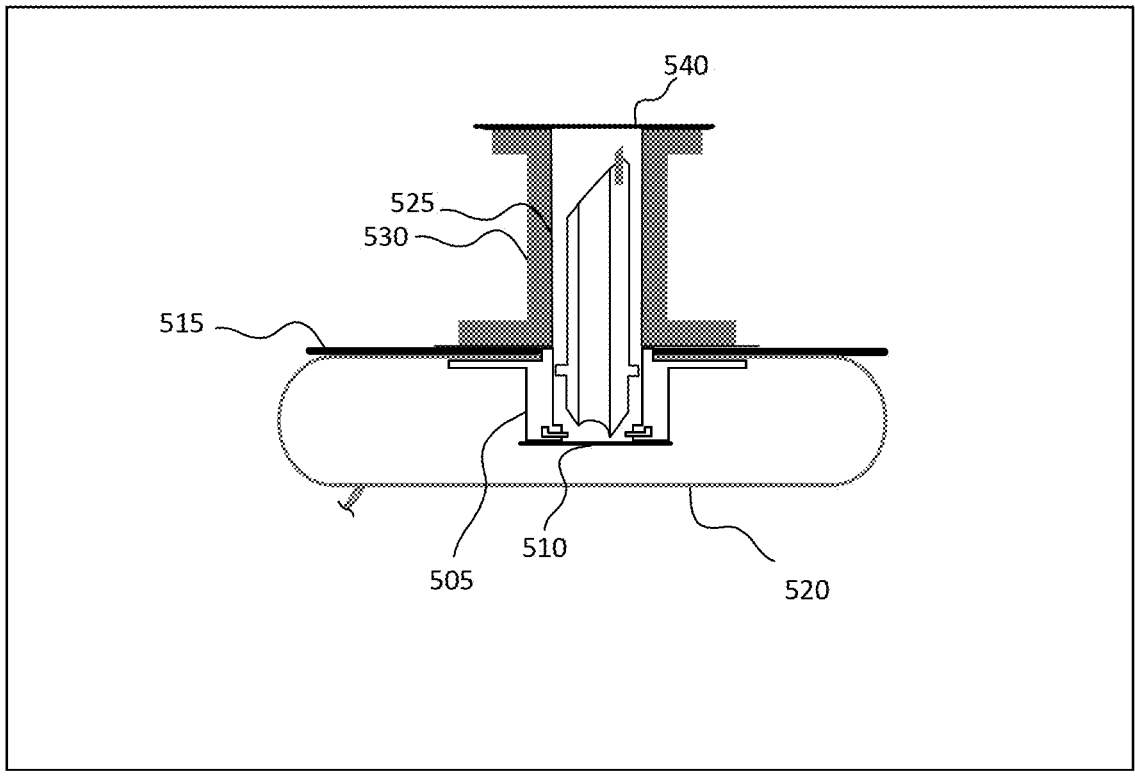
FIG. 10 illustrates another aspect of an embodiment of a method of manufacture of an autoinjector device for delivering a therapeutic preparation in fluid form.

In FIG. 10, a seal 540 is affixed to the collapsible tube 525 to complete a needle compartment that includes the bottom housing segment 505, the collapsible tube 525, the collar 530, the seal 510, and the seal 540.

The reservoir 520 is filled with a therapeutic preparation (e.g., containing a drug or other treatment) through a port (e.g., similar to the fill port 46 with the tube 44 in FIG. 1).

In an embodiment, the reservoir 520 is subjected to a vacuum to remove any gas within the reservoir 520 prior to filling the reservoir 520.

After filling the reservoir 520, the assembly illustrated in FIG. 10 can be further assembled into an autoinjector (e.g., any of the autoinjectors 10, 10A, 10B, 10C, 10D of FIG. 1, 2A, 2B, 2C, 2D, respectively, or other autoinjector design). For example, the pouch 32 containing the first reactant 38, the conduit 34, the second reactant 35, the release valve 36, the flap 24, and the deflation valve 28 of FIG. 1 may be incorporated with the assembly illustrated in FIG. 10 (where the balloon 515 of FIG. 10 is the balloon 12 of FIG. 1). The balloon 515 can then be sealed completely around its perimeter, such as by heat staking. The completed seal cuts off the port (e.g., the fill port 46) and seals the port tube (e.g., the tube 44). In an embodiment, after filling the reservoir 520, the port tube is sealed (e.g., by heat staking). Subsequently, the balloon 515 is sealed completely around its perimeter.

Reactants and associated assemblies may be added to the balloon 515 at any stage of the above manufacturing methodology. Further, the balloon 515 may be partially sealed at any stage of the above manufacturing methodology, with the seal completed at a subsequent stage.

In an embodiment, at least a portion of the components illustrated in FIGS. 5-10 are assembled within an isolator, and are sterilized prior to being brought into the isolator or are sterilized within the isolator. In this manner, the injection needle 535 can remain dry and sterile in the needle compartment that includes the bottom housing segment 505, the collapsible tube 525, the collar 530, the seal 510, and the seal 540, until the injection needle 535 is deployed and breaches the seal 510 and the seal 540. In an embodiment, after the assembly illustrated in FIG. 10 is complete, the port tube is sealed in the isolator, and the assembly is removed from the isolator (e.g., to a clean room) for completion of the device. In an embodiment, the assembly remains in the isolator for completion of the device.

In an embodiment, the needle compartment that includes the bottom housing segment 505, the collapsible tube 525, the collar 530, the seal 510, and the seal 540 is first assembled and then positioned through an opening defined by a membrane of the reservoir 520 to extend within the reservoir 520. The reservoir 520 is subsequently filled.

Embodiments can be used for the delivery of various preparations, including therapeutic preparations. The term "therapeutic preparation" refers herein to a preparation including one or more components where the preparation is intended for a therapeutic, diagnostic, or other biological purpose. Each therapeutic preparation can include one or more components, and a device or system can include one or more therapeutic preparations. A component of a therapeutic preparation can be, for example, a therapeutic agent such as a pharmacologically active agent, a DNA or SiRNA transcript, a cell, a cytotoxic agent, a vaccine or other prophylactic agent, a nutraceutical agent, a vasodilator, or a vasoconstrictor, or can be another type of component such as a delivery enhancing agent, a delay agent, an excipient, a diagnostic agent, or a substance for cosmetic enhancement.

A pharmacologically active agent can be, for example, an antibiotic, a nonsteroidal anti-inflammatory drug (NSAID), an angiogenesis inhibitor, a neuroprotective agent, a chemotherapeutic agent, a peptide, a protein, an immunoglobulin (e.g., a TNF-alpha antibody), an interleukin in the IL-17 family of interleukins, an anti-eosinophil antibody, another antibody, a nanobody, a large molecule, a small molecule, or a hormone, or a biologically active variant or derivative of any of the foregoing.

A cell can be, for example, a stem cell, a red blood cell, a white blood cell, a neuron, or other viable cell. Cells can be produced by or from living organisms or contain components of living organisms. A cell can be allogeneic or autologous.

A vaccine can be, for example, against an influenza, a coronavirus, meningitis, human papillomavirus (HPV), or chicken pox. A vaccine can correspond to an attenuated virus.

A nutraceutical agent can be, for example, vitamin A, thiamin, niacin, riboflavin, vitamin B-6, vitamin B-12, another B-vitamin, vitamin C (ascorbic acid), vitamin D, vitamin E, folic acid, phosphorous, iron, calcium, or magnesium.

A vasodilator can be, for example, I-arginine, sildenafil, a nitrate (e.g., nitroglycerin), or epinephrine.

A vasoconstrictor can be, for example, a stimulant, an amphetamine, an antihistamine, epinephrine, or cocaine.

A delivery enhancement agent can be, for example, a permeation enhancer, an enzyme blocker, a peptide that permeates through mucosa, an antiviral drug such as a protease inhibitor, a disintegrant, a superdisintegrant, a pH modifier, a surfactant, a bile salt, a fatty acid, a chelating agent, or a chitosan. A delivery enhancing agent can, for example, serve as a delivery medium for delivery of a component of a therapeutic preparation, or serve to improve absorption of a component of a therapeutic preparation into the body. A delivery enhancing agent can prime an epithelium of the intestine (e.g., fluidize an outer layer of cells) to improve absorption and/or bioavailability of one or more other components included in the delivery device.

A delay agent can be, for example, poly(lactic acid) (PLA), poly(glycolic acid) (PGA), polyethylene glycol (PEG), poly(ethylene oxide) (PEO), poly (I-lactic acid) (PLLA), poly(D-lactic acid) (PDLA), another polymer, or a hydrogel. A delay agent can be included with (e.g., mixed with, or providing a structure around) one or more other component(s) in a therapeutic preparation to slow a release rate of the other component(s) from the therapeutic preparation.

An excipient can be, for example, a binder, a disintegrant, a superdisintegrant, a buffering agent, an anti-oxidant, or a preservative. Excipients can provide a medium for a component of a therapeutic preparation (e.g., for assisting in manufacture), or to preserve integrity of a component of a therapeutic preparation (e.g., during manufacture, during storage, or after ingestion prior to dispersion within the body).

A diagnostic agent can be, for example, a sensing agent, a contrast agent, a radionuclide, a fluorescent substance, a luminescent substance, a radiopaque substance, or a magnetic substance.

A therapeutic preparation can include therapeutically effective amounts of a variety of therapeutic agents to treat a variety of diseases and conditions. Therapeutic agents include a number of large molecule peptides and proteins which would otherwise require injection due to chemical degradation and/or deactivation in the stomach or intestines. Examples include antibodies (e.g., including various monoclonal antibodies such as TNF-alfa antibodies), growth hormones (e.g., IGF and other growth factor), parathyroid hormones, interferons, immuno-chemotherapeutic agents, antibiotics, antivirals, insulin and related compounds, glucagon-like peptides (e.g., GLP-1, exenatide), anti-seizure agents (e.g., Furosemide), anti-migraine medications (e.g., sumatriptan), immune suppression agents (e.g., cyclosporine) and anti-parasitic agents (e.g., anti-malarial agents).

A dosage of a particular therapeutic agent can be titrated for a subject's weight, age or other parameter. A dosage to achieve a desired therapeutic effect as delivered into or through a GIW by way of an autoinjector of the present disclosure may be less than an amount that would be required for conventional oral delivery by way of absorption through a GIW. This is due in part to minimizing or preventing degradation of the therapeutic agent in biological matter or digestive matter, by protecting the fluid in a reservoir of the autoinjector until an instant of delivery of the fluid from the autoinjector to the GIW. In comparison, a therapeutic agent delivered by conventional oral delivery (e.g., a pill) can be largely degraded by biological matter or digestive matter prior to absorption; additionally, an absorption rate of a therapeutic agent delivered by conventional oral delivery may be low. Accordingly, a bioavailability of a therapeutic agent as delivered by conventional oral delivery may be low due to degradation and/or poor absorption (e.g., absolute bioavailability less than 5%, or less than 1%). Absolute bioavailability as used herein refers to bioavailability of an amount of therapeutic agent as delivered by the delivery mechanism under test (DMT) as compared to bioavailability of the same amount of the therapeutic agent as delivered by intravenous injection (IV), calculated by dividing area under the curve (AUC) of bioavailability by DMT to AUC of bioavailability of IV, presented as a percentage.

In an embodiment, an absolute bioavailability of a therapeutic agent as delivered by an autoinjector of the present disclosure is at least 95%. In an embodiment, an absolute bioavailability of a therapeutic agent as delivered by an autoinjector of the present disclosure is approximately 100%. In an embodiment, an absolute bioavailability of a therapeutic agent delivered by an autoinjector of the present disclosure is greater than 100%, because the therapeutic agent delivered by the autoinjector is retained within the body for a time (e.g., is delivered into the intestinal wall or peritoneal cavity, enters the blood stream over time, and is flushed out of the body), whereas the therapeutic agent delivered by IV is flushed out of the body more quickly (i.e., is delivered into the bloodstream and is flushed out of the body). The longer time spent by the therapeutic agent in the body can allow a longer time for the therapeutic agent to provide a therapeutic effect.

Depending on the therapeutic agent, a dose delivered by an autoinjector of the present disclosure can be in a range from 5% to 100% of a dose delivered by conventional oral delivery means to achieve a desired therapeutic effect. In an embodiment, a ratio of dosage by way of conventional oral delivery to dosage by way of autoinjector of the present disclosure is greater than 20:1. In an embodiment, a ratio of dosage by way of conventional oral delivery to dosage by way of autoinjector of the present disclosure is greater than 90:1.

Dose reduction provides benefits to a subject. For example, a potential toxicity and other side effects (e.g., gastric cramping, irritable bowel, hemorrhage, etc.) of a particular therapeutic agent alone or in combination with one or more other therapeutic agents delivered by an autoinjector of the present disclosure can be reduced because the delivered dose is lowered as compared to conventional oral delivery. This in turn improves compliance because the subject may have a reduction both in a severity and incidence of side effects. Additional benefits may include a reduced likelihood for a subject to develop a tolerance to the therapeutic agent and, in the case of antibiotics, for the subject to develop resistant strains of bacteria.

In addition to delivery of a single therapeutic agent, embodiments can be used to deliver multiple therapeutic agents for the treatment of multiple conditions or for multiple treatment prongs for a particular condition. In use, such embodiments allow a subject to forgo the necessity of having to take multiple medications for a particular condition or for multiple conditions.

Due to a difference in chemical makeup, molecular weight, or other parameter, therapeutic agents may be absorbed through the intestinal wall from the GI tract when delivered by conventional techniques (e.g., by pill) at different rates, resulting in different pharmacokinetic distribution curves. Embodiments address this issue by injecting the desired therapeutic agent mixtures at substantially the same time. This in turn may improve the pharmacokinetics and thus the efficacy of the selected mixture of therapeutic agents.

In various applications, embodiments can be used to deliver preparations including therapeutic agents to provide treatment for a number of medical conditions and diseases. The medical conditions and diseases which can be treated with embodiments can include without limitation: cancer, hormonal conditions (e.g., hypo/hyper thyroid, growth hormone conditions), osteoporosis, high blood pressure, elevated cholesterol and triglyceride, diabetes and other glucose regulation disorders, infection (local or septicemia), epilepsy and other seizure disorders, osteoporosis, coronary arrhythmia (both atrial and ventricular), coronary ischemia anemia or other like condition. Still other conditions and diseases are also contemplated such as various autoimmune disorders, including multiple sclerosis, Guillain-Barre syndrome, ankylosing spondylitis, chronic inflammatory demyelinating polyneuropathy, multifocal motor neuropathy, lupus and other conditions. Therapeutic agents for the latter conditions may include IgG and/or rituximab, among others.

In many embodiments, a treatment of the particular disease or condition using an autoinjector of the present disclosure can entirely replace other forms of treatment. In other embodiments, the treatment of the particular disease or condition using an autoinjector of the present disclosure can augment or reduce other forms of treatment.

As will be apparent from the description and drawings of the present disclosure, embodiments include without limitation:

An autoinjector including an inflatable balloon, a reservoir disposed within the inflatable balloon, a needle compartment attached to the balloon and to the reservoir; an injection needle disposed within the needle compartment; and an inflation mechanism. The reservoir contains a fluid therapeutic preparation comprising a therapeutic agent. The inflation mechanism is structured to inflate the balloon, wherein upon inflation of the balloon, the injection needle is structured to enter the reservoir at a proximal end of the injection needle.

A method of manufacture of an autoinjector includes: providing a needle compartment and a reservoir; sealing one end of the needle compartment; disposing the needle compartment partially within the reservoir; disposing an injection needle in a cavity defined by the needle compartment; and adding to the reservoir a fluid therapeutic preparation including a therapeutic agent.

A method includes making an autoinjector available to a subject with instructions to ingest the autoinjector. The autoinjector is structured to inject a fluid therapeutic preparation including a therapeutic agent into a wall of a gastrointestinal tract of the subject responsive to ingestion of the autoinjector. The autoinjector includes an injection needle disposed in a needle compartment attached to a reservoir, the injection needle being initially separated from the reservoir. The injection needle is structured to enter the reservoir for delivery of the fluid therapeutic preparation through the needle into the wall.

Any of the autoinjector or methods above, with any one of, or a combination of, the following features:

the reservoir is structured to hold up to 0.5 cc of fluid the reservoir contains 0.5 cc of fluid the device is structured to contain up to 50 milligrams of the therapeutic agent the therapeutic agent is one of two or more different therapeutic agents included in the therapeutic preparation an/the inflation mechanism includes two reactants, and the inflation mechanism is structured to keep the two reactants separate from each other until after the device encounters a fluidic environment the device is structured to deliver the therapeutic preparation through a wall of the gastrointestinal tract or through the wall and into the peritoneal cavity a fluid therapeutic preparation is passed through a port and into a tube fluidically coupled to the reservoir an end of the needle compartment to be disposed within the reservoir is sealed reactive to formation of gas within the autoinjector, a proximal end of the injection needle enters the reservoir and a distal end of the injection needle is exposed from the needle compartment to deliver the therapeutic preparation While the present disclosure has been described and illustrated with reference to specific embodiments thereof, these descriptions and illustrations do not limit the present disclosure. It can be clearly understood that various changes can be made, and equivalent components can be substituted within the embodiments, without departing from the true spirit and scope of the present disclosure as defined by the appended claims. Also, components, characteristics, or acts from one embodiment can be readily recombined or substituted with one or more components, characteristics or acts from other embodiments to form numerous additional embodiments within the scope of the invention. Moreover, components that are shown or described as being combined with other components, can, in various embodiments, exist as standalone components. Further, for any positive recitation of a component, characteristic, constituent, feature, step or the like, embodiments of the invention specifically contemplate the exclusion of that component, value, characteristic, constituent, feature, step or the like. The illustrations may not necessarily be drawn to scale. There can be distinctions between the artistic renditions in the present disclosure and the actual apparatus. There can be other embodiments of the present disclosure which are not specifically illustrated. The specification and drawings are to be regarded as illustrative rather than restrictive. Modifications can be made to adapt a particular situation, material, composition of matter, method, or process to the objective, spirit and scope of the present disclosure. All such modifications are intended to be within the scope of the claims appended hereto. While the methods disclosed herein have been described with reference to particular operations performed in a particular order, it can be understood that these operations can be combined, sub-divided, or re-ordered to form an equivalent method without departing from the teachings of the present disclosure. Therefore, unless specifically indicated herein, the order and grouping of the operations are not limitations of the present disclosure.

Various abbreviations may be used herein for standard units, such as deciliter (dl), milliliter (ml), microliter (μl), international unit (IU), centimeter (cm), millimeter (mm), nanometer (nm), inch (in), kilogram (kg), gram (gm), milligram (mg), microgram (μg), millimole (mM), degrees Celsius (° C.), degrees Fahrenheit (° F.), millitorr (mTorr), hour (hr), minute (min), or second (s or sec).

When used in the present disclosure, the terms "e.g.," "such as", "for example", "for an example", "for another example", "examples of", "by way of example", and "etc." indicate that a list of one or more non-limiting example(s) precedes or follows; it is to be understood that other examples not listed are also within the scope of the present disclosure.

As used herein, the singular terms "a," "an," and "the" may include plural referents unless the context clearly dictates otherwise. Reference to an object in the singular is not intended to mean "one and only one" unless explicitly so stated, but rather "one or more."

The term "in an embodiment" or a variation thereof (e.g., "in another embodiment" or "in one embodiment") refers herein to use in one or more embodiments, and in no case limits the scope of the present disclosure to only the embodiment as illustrated and/or described. Accordingly, a component illustrated and/or described herein with respect to an embodiment can be omitted or can be used in another embodiment (e.g., in another embodiment illustrated and described herein, or in another embodiment within the scope of the present disclosure and not illustrated and/or not described herein).

The term "component" refers herein to one item of a set of one or more items that together make up a device, formulation or system under discussion. A component may be in a solid, powder, gel, plasma, fluid, gas, or other form. For example, a device may include multiple solid components which are assembled together to structure the device and may further include a fluid component that is disposed in the device. For another example, a formulation may include two or more powdered and/or fluid components which are mixed together to make the formulation.

The term "design" or a grammatical variation thereof (e.g., "designing" or "designed") refers herein to characteristics intentionally incorporated based on, for example, estimates of tolerances (e.g., component tolerances and/or manufacturing tolerances) and estimates of environmental conditions expected to be encountered (e.g., temperature, humidity, external or internal ambient pressure, external or internal mechanical pressure, stress from external or internal mechanical pressure, age of product, or shelf life, or, if introduced into a body, physiology, body chemistry, biological composition of fluids or tissue, chemical composition of fluids or tissue, pH, species, diet, health, gender, age, ancestry, disease, or tissue damage); it is to be understood that actual tolerances and environmental conditions before and/ or after delivery can affect characteristics so that different components, devices, formulations, or systems with a same design can have different actual values with respect to those characteristics. Design encompasses also variations or modifications before or after manufacture.

The term "manufacture" or a grammatical variation thereof (e.g., "manufacturing" or "manufactured") as related to a component, device, formulation, or system refers herein to making or assembling the component, device, formulation, or system. Manufacture may be wholly or in part by hand and/or wholly or in part in an automated fashion.

The term "structured" or a grammatical variation thereof (e.g., "structure" or "structuring") refers herein to a component, device, formulation, or system that is manufactured according to a concept or design or variations thereof or modifications thereto (whether such variations or modifications occur before, during, or after manufacture) whether or not such concept or design is captured in a writing.

The term "body" refers herein to an animalia body.

The term "subject" refers herein to a body into which an embodiment of the present disclosure is, or is intended to be, delivered. For example, with respect to humans, a subject may be a patient under treatment of a health care professional.

The term "biological matter" refers herein to blood, tissue, fluid, enzymes, interstitial fluid, and other secretions of a body. The term "digestive matter" refers herein to biological matter along the GI tract in an animalia body, and other matter (e.g., food in an undigested or a digested form such as chyme) traversing the GI tract.

The term "ingest" or a grammatical variation thereof (e.g., "ingesting" or "ingested" or "ingestible") refers herein to taking into the stomach, whether by swallowing or by other means of depositing into the stomach (e.g., by depositing into the stomach by endoscope or depositing into the stomach via a port).

The term "degrade" or a grammatical variation thereof (e.g., "degrading", "degraded", "degradable", and "degradation") refers herein to weakening, partially degrading, or fully degrading, such as by dissolution, chemical degradation (including biodegradation), decomposition, chemical modification, mechanical degradation, or disintegration, which encompasses also, without limitation, dissolving, crumbling, deforming, shriveling, or shrinking. The term "non-degradable" refers to an expectation that degradation will be minimal, or within a certain acceptable design percentage, for at least an expected duration in an expected environment.

The terms "substantially" and "about" are used herein to describe and account for small variations. For example, when used in conjunction with a numerical value, the terms can refer to a variation in the value of less than or equal to ±10%, such as less than or equal to ±5%, less than or equal to ±4%, less than or equal to ±3%, less than or equal to ±2%, less than or equal to ±1%, less than or equal to ±0.5%, less than or equal to ±0.1%, or less than or equal to ±0.05%.

Additionally, amounts, ratios, and other numerical values may sometimes be presented herein in a range format. As used herein, a range of numbers includes any number within the range, or any sub-range if the minimum and maximum numbers in the sub-range fall within the range. It is to be understood that such range format is used for convenience and brevity and should be understood flexibly to include numerical values explicitly specified as limits of a range, but also to include all individual numerical values or sub-ranges encompassed within that range as if each numerical value and sub-range is explicitly specified. Thus, for example, "<9" can refer to any number less than nine, or any subrange of numbers where the minimum of the sub-range is greater than or equal to zero and the maximum of the sub-range is less than nine. Ratios may also be presented herein in a range format. For example, a ratio in the range of about 1 to about 200 should be understood to include the explicitly recited limits of about 1 and about 200, but also to include individual ratios such as about 2, about 3, and about 4, and sub-ranges such as about 10 to about 50, about 20 to about 100, and so forth.

The term "lumen" refers herein to the inside space of a tubular structure. Examples of lumens in a body include arteries, veins, and tubular cavities within organs.

The term "lumen wall" refers to a wall of a lumen, where the wall includes all layers from an inner perimeter to an outer perimeter of the lumen, such as, with respect to lumens in a body, the mucosa, submucosa, muscularis, serosa, and an outer wall of the lumen, with the constituent blood vessels and tissues.

The term "gastrointestinal tract" or "GI tract" refers herein to the intake/expulsion system of a body including, for example, the mouth, pharynx, esophagus, stomach, pylorus, small intestine, cecum, large intestine, colon, rectum, anus, and valves or sphincters therebetween.

What is claimed is:

1. A swallowable autoinjector device, comprising:
an inflatable balloon;
a reservoir disposed within the inflatable balloon, the reservoir containing a fluid therapeutic preparation comprising a therapeutic agent;
a needle compartment attached to the balloon and to the reservoir;
an injection needle disposed within the needle compartment; and
an inflation mechanism structured to inflate the balloon, wherein the injection needle is structured to enter the reservoir at a proximal end of the injection needle upon inflation of the balloon.

2. The device of claim 1, wherein the reservoir is structured to contain up to 0.5 cubic centimeters of fluid.

3. The device of claim 2, wherein the reservoir contains 0.5 cubic centimeters of fluid.

4. The device of claim 1, wherein the device is structured to contain up to 50 milligrams of the therapeutic agent.

5. The device of claim 1, wherein the therapeutic agent comprises two or more different therapeutic agents included in the therapeutic preparation.

6. The device of claim 1, wherein the inflation mechanism comprises a first reactant and a second reactant, and the inflation mechanism is structured to keep the first and second reactants separate from each other until after the device encounters a fluidic environment, wherein the first reactant and second reactant are selected to react with each other to cause a gas to form and thereby inflate the balloon.

7. The device of claim 6, further comprising a pouch contained within an inner volume of the balloon, the pouch containing the first reactant and being in fluid communication with a conduit, the conduit being in fluid communication with both an inside volume of the pouch and an inner volume of the balloon containing the second reactant, and a release valve disposed between the pouch and the conduit, the release valve being configured to degrade upon contact with a fluidic environment.

8. The device of claim 6, wherein the reservoir comprises a membrane configured to be compressed by the gas generated by reaction of the first and second reactants and thereby cause the fluid therapeutic preparation to flow from the reservoir into the injection needle.

9. The device of claim 1, wherein the device is structured to deliver the therapeutic preparation through a wall of the gastrointestinal tract or through the wall and into the peritoneal cavity.

10. The device of claim 1, further comprising a deflation valve configured to deflate the balloon after the fluid therapeutic composition has been expelled from the reservoir.

11. The device of claim 10, wherein the deflation valve is covered with a flap when the balloon is in a non-inflated state.

12. The device of claim 1, further comprising a sizing member configured to contact a portion of a gastrointestinal tract wall and urge an opposing side of the balloon against another portion of the gastrointestinal tract wall.

13. The device of claim 1, wherein the needle compartment comprises an upper chamber and a lower chamber, the upper chamber including a collar and a collapsible tube configured to protect and support the injection needle, wherein the collar is at least partially formed of a material that degrades upon exposure to a fluidic environment.

14. The device of claim 1, wherein the injection needle has a tubular shape with a central channel extending between a distal end and the proximal end, wherein the distal end terminates at a sharp tip.

15. The device of claim 1, wherein the injection needle comprises biodegradable material.

16. The device of claim 1, further comprising a fill port coupled to the reservoir.

17. The device of claim 1, wherein the device is contained within a capsule that degrades within the gastrointestinal tract.

18. The device of claim 1, wherein the therapeutic agent comprises one or more selected from antibodies, growth hormones, parathyroid hormones, interferons, immuno-chemotherapeutic agents, antibiotics, antivirals, insulin and related compounds, glucagon-like peptides, anti-seizure agents, anti-migraine medications, immune suppression agents, and anti-parasitic agents.

19. A method of manufacturing the swallowable autoinjector device of claim 1, the method comprising:
providing the needle compartment and the reservoir;
sealing one end of the needle compartment;
disposing the needle compartment partially within the reservoir;
disposing the injection needle in a cavity defined by the needle compartment, wherein the injection needle is structured to enter the reservoir at a proximal end of the injection needle; and
adding to the reservoir the fluid therapeutic preparation.

20. The method of claim 19, further comprising disposing the reservoir containing the fluid therapeutic preparation and the needle compartment containing the injection needle within the inflatable balloon.

21. A method of administering a therapeutic agent to a subject in need thereof, comprising orally administering a capsule containing the device of claim 1.

* * * * *